United States Patent

Briggs

[11] Patent Number: 5,183,907
[45] Date of Patent: Feb. 2, 1993

[54] PROCESS FOR PREPARING DIPHENYL ETHERS

[75] Inventor: Stuart P. Briggs, Faversham, England

[73] Assignee: Shell Internationale Research Maatschappij B.V., The Hague, Netherlands

[21] Appl. No.: 784,743

[22] Filed: Oct. 29, 1991

Related U.S. Application Data

[63] Continuation of Ser. No. 241,196, Sep. 7, 1988, abandoned.

[30] Foreign Application Priority Data

Sep. 30, 1987 [GB] United Kingdom ............... 8722968

[51] Int. Cl.$^5$ ........................................... C07D 307/88
[52] U.S. Cl. ................................................. 549/310
[58] Field of Search ........................................ 549/310

[56] References Cited

U.S. PATENT DOCUMENTS 4,298,530 11/1981 Iwasaki et al. .................. 549/310

FOREIGN PATENT DOCUMENTS 50-84563 7/1975 Japan.

OTHER PUBLICATIONS

Organic Reactions vol. 15, chapter 2, pp. 206, 210, John Wiley & Sons, Inc.

Primary Examiner—Jane T. Fan

[57] ABSTRACT

Diphenyl ether derivatives of formula II

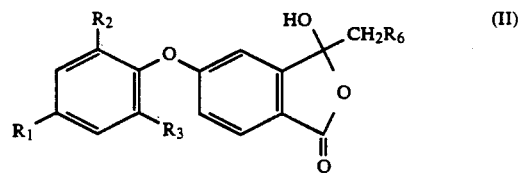

wherein $R_1$ represents a hydrogen or halogen atom or an alkyl or haloalkyl group, $R_2$ and $R_3$, which may be the same or different, each independently represents a hydrogen or halogen atom, or an alkyl, haloalkyl, nitro or cyano group, and $R_6$ represents a hydrogen atom or an alkyl group, useful as intermediates in the preparation of diphenyl ether herbicides, are prepared by treating a compound of formula III

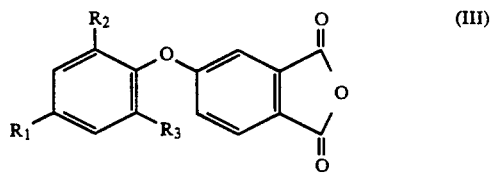

where $R_1$, $R_2$ and $R_3$ are as defined above with a dicarboxylic acid of formula $R_6$—$CH(COOH)_2$, where $R_6$ is as defined above, in the presence of an organic base.

9 Claims, No Drawings

PROCESS FOR PREPARING DIPHENYL ETHERS

This application is a continuation-in-part of application Ser. No. 07/241,196, filed Sep. 7, 1988, now abandoned.

This invention relates to a process for preparing diphenyl ether derivatives and the use of such derivatives as intermediates in the preparation of certain diphenyl ether herbicides.

The applicants' copending UK Patent Application No. 8720509 describes and claims herbicidal phenoxy phthalide derivatives having the general formula I:

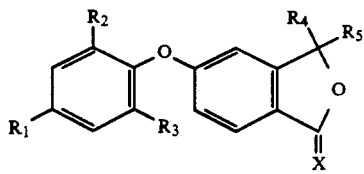

wherein $R_1$ represents a hydrogen or halogen atom, preferably chlorine, or an alkyl or haloalkyl group, suitably of 1-4 carbon atoms, preferably trifluoromethyl; $R_2$ and $R_3$, which may be the same or different, each independently represents a hydrogen or halogen atom, preferably chlorine, or an alkyl or haloalkyl group, suitably of 1-4 carbon atoms, for example trifluoromethyl, or a nitro or cyano group; $R_4$ represents a saturated alkyl group; $R_5$ represents an unsaturated alkyl group; and X represents an oxygen or sulphur atom.

The applicants' copending European Patent Application Publication No. 219144 similarly describes and claims herbicidal phenoxy phthalide derivatives having the formula (I) above where X is oxygen and $R_4$ and $R_5$, which may be the same or different, each independently represents an alkyl group.

The synthesis of such derivatives, especially where $R_4$ and $R_5$ are not identical, can be complex. Thus for example, in accordance with the above mentioned EP-A-21944, the synthesis of a compound when $R_4$ is methyl and $R_5$ is ethyl is carried out by first reacting the corresponding 3-hydroxy phthalide (i.e. a compound of formula I where $R_4$ is hydrogen and $R_5$ is hydroxy) with a Grignard reagent (e.g. methyl magnesium bromide) to give the 3-methyl phthalide and then reacting the product with an alkyl halide (e.g. iodoethane) in the presence of lithium diisopropylamine to give the desired 3-methyl-3-ethyl phthalide.

According to the present invention we provide a process for the preparation of a diphenyl ether derivative of formula II

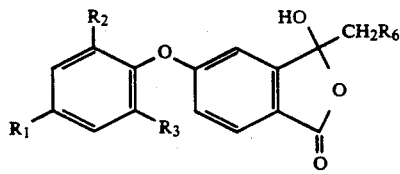

wherein $R_1$ represents a hydrogen or halogen atom, preferably chlorine, or an alkyl or haloalkyl group, suitably of 1-4 carbon atoms, preferably trifluoromethyl; $R_2$ and $R_3$, which may be the same or different, each independently represents a hydrogen or halogen atom, preferably chlorine, or an alkyl or haloalkyl group, suitably of 1-4 carbon atoms, for example trifluoromethyl, or a nitro or cyano group; and $R_6$ represents a hydrogen atom or an alkyl group, preferably having up to 4 carbon atoms, preferably methyl, comprising treating a compound of formula III

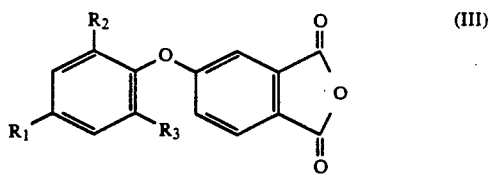

where $R_1$, $R_2$, and $R_3$ are as defined above with a dicarboxylic acid of formula $R_6$—CH(COOH)$_2$, where $R_6$ is as defined above, in the presence of an organic base.

The dicarboxylic acid is preferably malonic acid giving a compound of formula II where $R_6$ is hydrogen.

The organic base may be an aliphatic base such as triethylamine, an aromatic carboxylic base such as N,N-dimethyl aniline, or an aromatic heterocyclic base such as pyridine. The base preferably acts as solvent for the reaction.

The reactants are preferably employed using in excess of 1 mole equivalent of dicarboxylic acid per mole of compound of formula III, for example in a molar ratio of 1 to 2 mole equivalents of acid per mole of anhydride. The reaction temperature is preferably from room temperature to 100° C., or lower dependent on the decomposition point of the dicarboxylic acid employed. A preferred reaction temperature is from 70° to 90° C., preferably about 80° C. with a reaction time of about 5 hours.

The reaction may be followed by any necessary separation procedures such as chromatography and/or recrystallisation from, for example, petrol/diethyl ether to remove unwanted isomeric by-products due to reaction with the second carbonyl group of the anhydride III. However in practice it has usually been found that the desired compound of formula II is obtained as the major product.

The anhydrides of formula III are known for example from U.S. Pat. No. 4,334,915. They may be prepared for example by reaction of a compound of 3,4-dimethylphenol with a substituted halobenzene followed by oxidation of the methyl groups to acid groups and ring closure to form the anhydrides of formula III.

The invention also includes compounds of formula II when prepared by the process described above.

Compounds of formula II above are valuable intermediates for the preparation of compounds of formula I. Their use in the preparation of compounds of formula I where $R_4$ represents a saturated alkyl group and $R_5$ represents an unsaturated alkyl group is described and claimed in our copending UK Patent Application No. 8720509. They are however also valuable in the preparation of compounds of formula I where $R_4$ and $R_5$, which may be the same or different, each independently represents an alkyl group.

Thus according to a further aspect of this invention we provide a process for the preparation of a compound of formula I where $R_4$ represents the group —CH$_2$R$_6$ and $R_5$ represents a saturated or unsaturated alkyl group comprising reacting a compound of formula II which has been prepared as described above with an organometallic compound of formula $R_5$-M-Hal where M represents a metal atom and Hal represents a halogen atom, and optionally converting the compound of formula I where X represents an oxygen atom to a compound of formula I where X represents a sulphur atom.

The moiety Hal may be a chlorine, bromine or iodine atom.

The organometallic reagent used is preferably an organomagnesium compound (Grignard reagent), which may be prepared according to established procedures, e.g. by taking up the appropriate alkyl halide and magnesium metal in an aliphatic ether, such as diethyl ether in the absence of water. The reaction of the compound of formula II with that Grignard reagent is suitably carried out in a solvent, which may also be diethyl ether, or may be a different inert organic solvent such as tetrahydrofuran. The formation of the Grignard reagent and its reaction with the compound of formula II are each suitably carried out at ambient temperatures, although temperatures up to the boiling point of the solvent used may be employed. The Grignard organomagnesium complex may be supplemented by the generation of an organocadmium complex through the addition of cadmium chloride.

The invention also includes compounds of formula I when prepared by the process defined above.

Preferably in the compound of formula I, $R_1$ is trifluoromethyl, $R_2$ is a chlorine atom, $R_3$ is hydrogen, X is oxygen, $R_4$ is a methyl group and $R_5$ is an ethyl group, a vinyl group or an ethynyl group.

The invention is illustrated in the following Examples.

EXAMPLE 1

5-(2-chloro-4-trifluoromethylphenoxy)-phthalic anhydride a) Sodium hydroxide (740g, 18.5mol), 3,4-dimethylphenol (2255 g, 18.5 mol) and sulpholane (7.51) were mixed and stirred at room temperature for 1 hour. Petroleum ether b.p. 100°-120° C. (21) was added and the mixture heated to reflux and water removed by azeotropic distillation. After 7 hours further sodium hydroxide (74 g, 1.85 mol) was added and refluxing continued until water ceased distilling over. 3-chloro-4-fluorobenzotrifluoride (3672 g, 18.5 mol) was added at 80°-90° C. After completion of the reaction and cooling, the reaction mixture was poured into cold water and the organic layer separated. After washing with sodium hydroxide and water the organic phase was concentrated to yield an oil (5178 g.) distilling at 0.2 mm Hg/120° C.

b) The product of step a) (300.5 g, 1.0 mol) in acetic acid (600 ml) and acetic anhydride (26 ml) was mixed with cobalt acetate (9 g, 0.036 mol) and cobalt bromide (6 g, 0.018 mol). The mixture was stirred, heated to 100° C. and oxygen passed through at about 2 l.min$^{-1}$. After the exothermic reaction subsided, solvent was removed by distillation and the residue triturated with toluene to give a white solid (239 g) m.p. 170°-170° C.

c) Product obtained as in step b (730 g, 2.03 mol) in xylene (2.51) was heated under reflux and water removed by azeotropic distillation. After 6 hours reflux the mixture was cooled, filtered and xylene removed by distillation to give a yellow oil which crystallised from petroleum spirit.

Yield of the title compound 624 g. m.p. 88°-91° C.

EXAMPLE 2

Preparation of 5-(2-chloro-4-trifluoromethylphenoxy)-3-hydroxy-3-methylphthalide Dried malonic acid (156 g, 1.5 mol) and 5-(2-chloro-4-trifluoromethylphenoxy)phthalic anhydride (342 g, 1.0 mol) were stirred with triethylamine (200 ml) under a nitrogen atmosphere and warmed slowly to 80° C. After 5 hours at 80° C., the reaction mixture was allowed to cool to room temperature and ethyl acetate (750 ml) and water (500 ml) were added. The organic phase was separated and washed with dilute hydrochloric acid then water. Ethyl acetate was distilled from the solution and the crude product purified by chromatography over silica gel. Finally, crystallisation from 40°-60° petroleum spirit/diethyl ether afforded the product as a white solid, m.p. 106°-108° C. Yield=154 g (43%).

Analysis: Calculated %: C 53.58; H 2.81
Found %: C 53.7; H 2.8 .

EXAMPLE 3

Preparation of 5-(2-chloro-4-trifluromethylphenoxy)-3-methyl-3-vinyl phthalide

Vinyl bromide (112.4 g, 1.05 mol) in THF (500 ml) was added to magnesium (24 g, 1.0 mol) in THF (500 ml) under a nitrogen blanket over 1 hour. The temperature was maintained below 60° during addition and stirring continued for a further 30 minutes during which all the magnesium dissolved. The reaction mixture was cooled to 0° C. and then a solution of 5-(2-chloro-4-trifluoromethylphenoxy)-3-hydroxy-3-methylphthalide, prepared as described in Example 2, (119.5 g, 0.33 mol) in THF (500 ml) was run in while maintaining a temperature of 0° to 5° C. After stirring for a further 1 hour, during which the temperature rose to 20° C., dilute hydrochloric acid (1.1 mol in 250 ml) was added very cautiously over 30 minutes. The solution separated into two layers and the aqueous layer was run off. Toluene (500 ml) was added and the solution washed twice with water. The solvent was stripped and the residual oil dissolved in ethyl acetate/60°-80° petroleum spirit and eluted over silica. The desired product, 5-(2-chloro-4-trifluoromethylphenoxy)-3-methyl-3-vinyl phthalide, was crystallised from hexane, m.p.=71°-73° C. Yield=122.2 g (96%).

Analysis: Calculated %: C 58.63; H 3.28
Found %: C 58.5; H 3.3.

EXAMPLE 4

Preparation of 5-(2-chloro-4-trifluoromethylphenoxy)-3-ethyl-3-methylphthalide

Magnesium (1.44 g, 0.06 mol) suspended in diethyl ether (20 ml), was treated with a crystal of iodine, then a solution of bromoethane (6.54 g, 0.06 mol) in diethyl ether (15 ml) was added dropwise over 30 minutes. Reflux was maintained throughout this period by the heat of reaction. The mixture was stirred for 45 minutes before a solution of 5-(2-chloro-4-trifluoromethylphenoxy)-3-hydroxy-3-methylphthalide (5.38 g, 0.015 mol) dissolved in diethyl ether (20 ml) was added over 20 minutes. After stirring for a further 40 minutes, 50% hydrochloric acid (12 ml) was cautiously added, then the phases separated. The organic phase was washed with water 3×15 ml), the solvent stripped off and the residual oil distilled.

Yield of pale yellow oil=4.9 g (88%).
Analysis: Found %: C 58.7; H 3.9
Calculated %: C 58.3; H 3.9.

EXAMPLE 5

Preparation of 5-(2-chloro-4-trifluoromethylphenoxy)-3-ethyl-3-hydroxyphthalide Dried 2-methylmalonic acid (2.07 g, 0.0175 mol) and 5-(2-chloro-4- trifluoromethylphenoxy) phthalic anhydride (4 g, 0.0117 mol) were stirred with triethylamine (2.36 g, 0.0234 mol) and warmed slowly to 75° C. After 5 hours at 75° C. the reaction mixture was allowed to cool to room temperature and ethyl acetate (50 ml) and water (20 ml) were added. The organic phase was separated, then washed with dilute hydrochloric acid and then water. Solvent was distilled from the organic solution and the residue was eluted over silica gel with a mixture of ethyl acetate/petroleum spirit. The desired product crystallised from hexane/diethyl ether. Yield=2.0 g (46%). mp 120°-122.5° C.

I claim:

1. A process for the preparation of a diphenyl ether derivative of Formula II

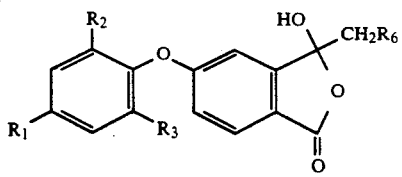

wherein $R_1$ represents a hydrogen or halogen atom or an alkyl or haloalkyl group, $R_2$ and $R_3$, which may be the same or different, each independently represents a hydrogen or halogen atom, or an alkyl, haloalkl, nitro or cyano group, and $R_6$ represents a hydrogen atom or an alkyl group, said process comprising treating a compound of formula III

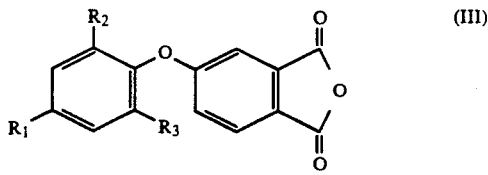

where $R_1$, $R_2$ and $R_3$ are as defined above with a dicarboxylic acid of formula $R_6$—$CH(COOH)_2$, where $R_6$ is as defined above, in the presence of an organic base, to obtain a reaction mixture containing product of formula II as the major product, and separating the product of the formula II from the reaction mixture.

2. A process according to claim 1 wherein a compound of formula II is prepared in which $R_1$ is $CF_3$, $R_2$ is chlorine and $R_3$ is hydrogen.

3. A process according to claim 1 or 2 wherein a compound of formula II is prepared in which $R_6$ is a hydrogen atom.

4. A process according to claim 1 or 2 wherein the dicarboxylic acid is malonic acid.

5. A process according to claim 1 or 2 wherein the organic base is selected from the group consisting of triethylamine and pyridine.

6. A precess according to claim 5 wherein the organic base acts as the reaction solvent.

7. A process according to claim 6 wherein the reaction temperature ranges from 70° C. to 80° C.

8. A process according to claim 6 wherein the time of reaction is up to about 5 hours.

9. A process according to claim 7 wherein $R_6$ is a hydrogen atom or a methyl group.

* * * * *